(12) United States Patent
Manalis et al.

(10) Patent No.: US 8,631,685 B2
(45) Date of Patent: Jan. 21, 2014

(54) METHOD AND APPARATUS FOR EXTENDED TIME AND VARYING ENVIRONMENT MEASUREMENTS OF SINGLE PARTICLES IN MICROFLUIDIC CHANNELS

(75) Inventors: Scott Manalis, Cambridge, MA (US); Andrea K. Bryan, Allston, MA (US); Michel Godin, Beaconsfield (CA); Philip Dextras, Tokyo (JP); Sungmin Son, Boston, MA (US); Thomas Burg, Goettingen (DE); William Grover, Medford, MA (US); Yao-Chung Weng, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 744 days.

(21) Appl. No.: 12/661,772

(22) Filed: Mar. 23, 2010

(65) Prior Publication Data
US 2010/0288043 A1   Nov. 18, 2010

Related U.S. Application Data

(63) Continuation-in-part of application No. 12/587,898, filed on Oct. 14, 2009, now Pat. No. 8,312,763.

(60) Provisional application No. 61/105,619, filed on Oct. 15, 2008.

(51) Int. Cl.
*G01N 15/10*   (2006.01)

(52) U.S. Cl.
USPC .................. 73/61.75; 73/61.71; 73/61.73

(58) Field of Classification Search
USPC ............................. 73/61.73, 61.75
See application file for complete search history.

(56) References Cited

U.S. PATENT DOCUMENTS

2009/0136982 A1 *  5/2009  Tang et al. ................ 435/29

* cited by examiner

*Primary Examiner* — Hezron E Williams
*Assistant Examiner* — Paul West
(74) *Attorney, Agent, or Firm* — Mark Rodgers

(57) ABSTRACT

Methods and apparatus for improving measurements of particle or cell characteristics, such as mass, in Suspended Microchannel Resonators (SMR's). Apparatus include in particular designs for trapping particles in SMR's for extended measurement periods and for changing the fluid properties within the SMR during the extended periods. Methods include techniques to provide for cell growth over time and over time in response to changing fluid properties to aid in determining parameters such as drug resistance and drug susceptibility.

2 Claims, 10 Drawing Sheets

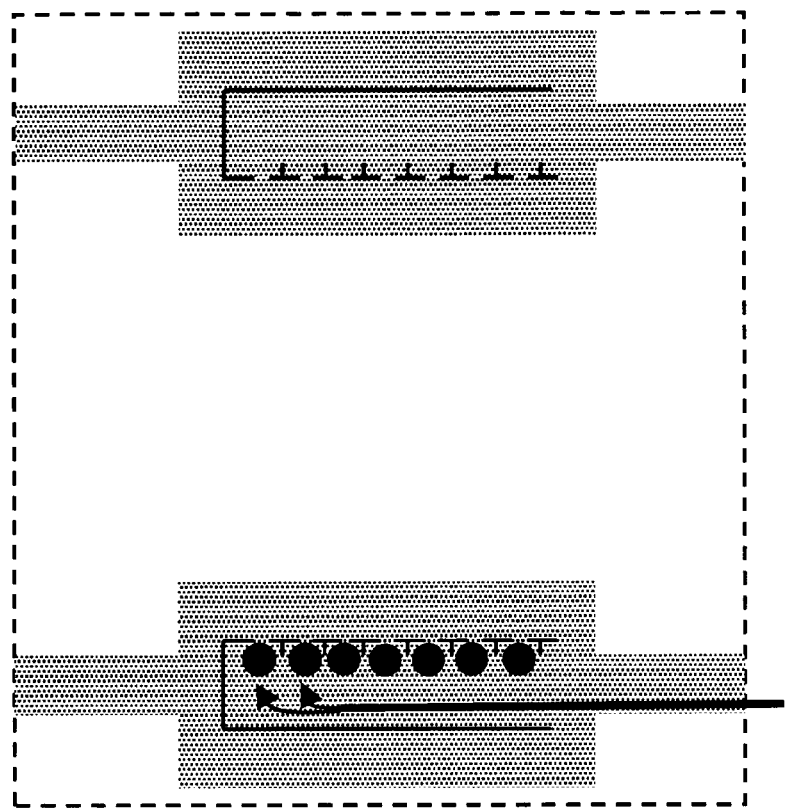
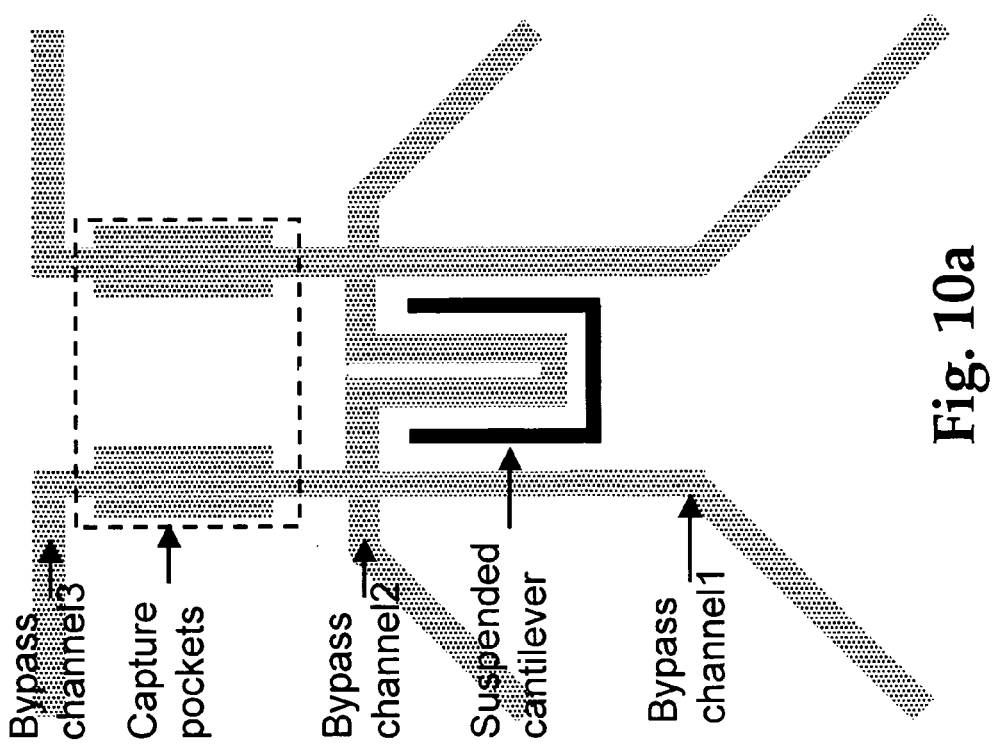
Fig. 10b
Bypass channel3
Capture pockets
Bypass channel2
Suspended cantilever
Bypass channel1
Fig. 10a

METHOD AND APPARATUS FOR EXTENDED TIME AND VARYING ENVIRONMENT MEASUREMENTS OF SINGLE PARTICLES IN MICROFLUIDIC CHANNELS

RELATED APPLICATIONS

This application is a Continuation-in-Part of application U.S. Ser. No. 12/587,898, filed Oct. 14, 2009, now U.S. Pat. No. 8,312,763 which claims priority to U.S. provisional application 61/105,619, filed Oct. 15, 2008

FEDERALLY SPONSORED RESEARCH

National Institutes of Health (NIH) R01GM085457
Institute for Collaborative Biotechnologies from the U.S. Army Research Office

BACKGROUND OF THE INVENTION

This invention relates to methods and apparatus for measuring a property such as mass, size or density of target particles, and more particularly to such measurements using a Suspended Microchannel Resonator (SMR) and measuring the change in such properties over time and in changing environments.

Precision measurements of nanometer- and micrometer-scale particles, including living cells, have wide application in pharmaceuticals/drug delivery, disease studies, paints and coatings, foods, and other major industries and fields of research. This need is growing due to the expanding use of particulate engineering across these industries, to emerging nano- and micro-particle manufacturing techniques, to the need to better understand and treat diseases, and to recent regulations governing quality control in the pharmaceutical industry.

A variety of particle sizing and counting techniques, such as light scattering, Coulter Counters and others are known in the art. These techniques are embodied in commercial instruments and are used in industrial, medical, and research applications. Although such techniques have proven utility, they have limitations, which limit their applicability. Relatively recently, particle detection and measurement based on the use of SMR's has been developed, and shows promise of going beyond some of the limitations of conventional techniques. The SMR uses a fluidic microchannel embedded in a resonant structure, typically in the form of a cantilever or torsional structure. Fluids, possibly containing target particles are flowed through the sensor, and the contribution of the flowed material to the total mass within the sensor causes the resonance frequency of the sensor to change in a measurable fashion. SMR's are typically microfabricated MEMS devices. The use of microfabricated resonant mass sensors to measure fluid density has been known in the literature for some time [P. Enoksson, G. Stemme, E. Stemme, "Silicon tube structures for a fluid-density sensor", Sensors and Actuators A 54 (1996) 558-562]. However, the practical use of resonant mass sensors to measure properties of individual particles and other entities suspended in fluid is relatively recent, as earlier fluid density sensors were not designed to measure individual particles at the micron and submicron scale.

In a body of work by common inventors and owned by the assignee of the current application, miniaturization and improvement of several orders of magnitude in mass resolution has been demonstrated. Development in the microfabrication recipes, the fluidics design, and measurement techniques are described in a number of co-pending patent applications and scientific publications. In particular U.S. patent application Ser. Nos. 11/620,320, 12/087,495, and 12/305,733 are particularly relevant and are incorporated by reference in their entirety. Also of relevance is a publication by some of the current inventors, [T. P. Burg, M. Godin, S. M. Knudsen et al., "Weighing of biomolecules, single cells and single nanoparticles in fluid," Nature 446 (7139), 1066-1069 (2007)] By using the microfabrication techniques described in the references, SMR sensors have been fabricated with mass resolution of less than 1 femtogram ($10^{-15}$ g). This resolution is sufficient to detect and measure the mass of individual particles in the range of ~100 nanometers up to many microns in size, including mammalian cells.

Improvements in SMR based measurement techniques have been disclosed, particularly in the parent application of this application, allow for a particle to remain in the measurement portion of the SMR for extended periods of time. Although the disclosed techniques have the advantage of improving signal to noise, they also provide for the ability to measure particle properties which may change over time. Of particular interest is the possibility of measuring cell growth. High precision measurements of the mass of living cells have not been possible previously. Three methods are commonly used to measure cell size and none can measure mass. In the first, cross-sectional areas derived from focused microscope images are used to estimate cell volume, through either integration of a series or assumption of a simple shape (e.g. a sphere). In the second, the forward scatter (FSC) of light by cells is measured. In the third, a particle analyzer, the Coulter Counter, uses volume displacement of an electrolyte to measure cell volume. The first two approaches suffer from a lack of precision and in addition, FSC measurements are not based on an absolute scale. Nor is it clear how linear the relationship between FSC and cell size actually is, or how dependent FSC is on additional physical properties. The third approach (volume displacement) is the most effective but requires the dangerous assumption that mass density is constant. Eukaryotic cell volume and hence mass density can change quickly by altering ion balance. Even in cells with rigid cell walls (e.g. yeast), mass density depends on the proportion of volume occupied by large fluid-filled vacuoles, a proportion sensitive to environmental and genetic alterations.

Given the mass resolution of current SMR's cell mass measurements potentially may be accomplished at very high resolution, for a single mammalian cell approximately 0.01%, which is orders of magnitude better than what could be achieved with existing optical methods. With such resolution it is possible to measure cell mass change over time and potentially even more importantly in response to changes in the chemical or environmental properties of the cell's liquid environment. Such measurements would have applicability in drug resistance/susceptibility studies, and general environmental toxicity studies. For example, clinical oncology and cancer biology are challenged by the lack of assay platforms for measuring changes in cancer-cells' growth kinetics in response to chemical therapeutic intervention. Therefore it is the object of this invention to disclose methods and apparatus for extended time measurements of particles in an SMR along with methods and apparatus to change the chemical or environmental properties of the fluids in extended time measurements.

SUMMARY OF THE INVENTION

The invention, in one embodiment is a Suspended Microchannel Resonator (SMR) system including at least one fluid channel disposed between two independently pressure controlled ports and a particle trap. Various traps include: (1) feedback means between an oscillation detector and the pressure control of one or more ports such that a substantially maximum effect on the SMR oscillation is detected due to a particle traveling through the fluid channel and thereafter each time a predetermined decrease from the maximum is detected, the pressure differential on the two ports is reversed to trap the particle within a sensitive measurement region of the SMR; (2) feedback means between a optical detector such as Charge Coupled Device, Photodiode, or Photo Multiplier Tube that monitors the particle motion inside the fluid channel and the pressure control of one or more ports. (3) a post trap; (4) an optical tweezer trap, optically trapping a particle in the sensitive measurement region of the SMR; (5) an inertial trap which inertially traps a particle in the sensitive measurement area of the SMR by at least one of reducing fluid flow or increasing oscillation amplitude; and (6) a pocket trap in a third pressure controlled channel in fluid communication with the first channel.

The SMR system may also include a fluidic delivery element disposed to modify the fluidic environment during the time period in which the particle is trapped. In a particular version, the delivery element may be an additional channel with an independent port in fluid communication with the first fluid channel, such that fluid introduced in the additional channel mixes with the fluid in the first channel to change the fluid environment during the period when the particle is trapped.

In another embodiment, the invention is an SMR with a fluid channel, at least partially on the resonant portion of the SMR and at least one additional channel including at least one particle capture pocket in fluid communication with the first channel, and independent pressure control of all channel ports. Particles are introduced into the channels, and through pressure control and fluid composition, particles are trapped in the pocket for a period of time during which the fluid environment in the pocket may be varied, and subsequently released into the resonant portion of the SMR for measurement purposes. The particle may be recaptured and exposed to possibly different fluid environments and then re-measured. Thus both time and environment can be varied in the pocket(s) in between measurement trips through the resonant SMR channel.

In another embodiment, the invention is a Method for measuring cell growth using an SMR with a particle trap, including the steps of introducing at least one cell into the SMR, trapping a cell in the particle trap, and measuring the change in mass of the cell during at least one of the period in which it is trapped and before/after it is trapped.

In a another embodiment, the method further includes changing the properties of the fluid, including, chemical and environmental properties, during at least one of the period when the cell is trapped in the SMR or the period when a subsequent cell is trapped in the SMR. Measuring the change in mass (and/or density) over time in response to the change in fluid properties, may aid in determining parameters such as drug resistance and drug susceptibility.

The methods may also include calibrating for changes in density in the fluid if required.

BRIEF DESCRIPTION OF THE DRAWINGS

The invention will be better understood by referring to the following figures:

FIG. 10 depicts trapping the cell external to the oscillated portion of the SMR.

DETAILED DESCRIPTION OF THE INVENTION

The embodiments described herein are improved apparatus and methods that can be implemented using the microfabrication techniques, fluidics, and control electronics disclosed in the documents referenced and other publications available at the time the invention was made. Since those aspects of the invention do not contribute to the novelty, they are not described in detail. For instance novel versions of the SMR's may be produced with mask changes in the microfabrication process. Similarly the fluidics, data acquisition, and data processing steps can be accomplished with implementations derived from set-ups previously disclosed. The novelty of the current invention lies in the arranging of the physical SMR geometries, fluid control schemes and measurement steps to achieve significantly improved results. Also the term particle is interchangeably used in this application to mean any particulate substance, including cells, and particularly live cells in a suitable carrier fluid. Thus particular embodiments may be described in terms of cells and others in terms of particles, but it is to be understood that no embodiments herein disclosed are restricted to a particular type of particle. For instance material directed to cell growth may be applicable to other particles whose mass changes over time in a carrier fluid. Also it is to be understood that fixed end cantilever SMR's are shown by way of example, but the techniques disclosed are not restricted to any particular geometry.

A variety of SMR geometries and fluidic schemes are disclosed for the purposes of trapping particles in a sensitive measurement region of an SMR along with measurement techniques that can be employed in trapping-capable SMR set-ups. If single cells are trapped at the mass sensitive region of the SMR the mass and density can be measured versus time and the fluidic environment of the cell, so that growth can be perturbed by the delivery of various analytes.

Figure 1:
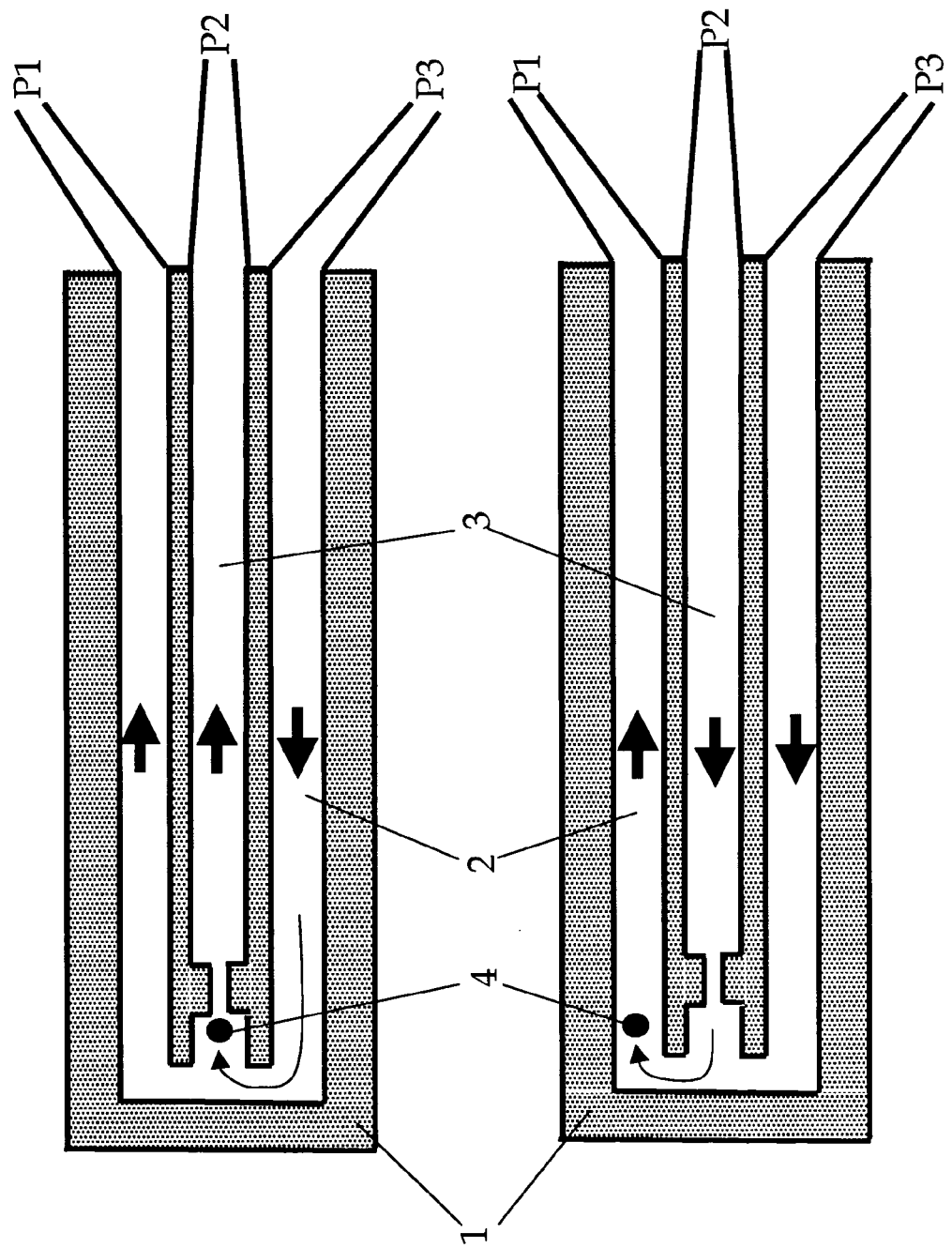
FIG. 1 is a schematic illustration of a Suspended Microchannel Resonator configured with an additional channel and particle trap.

Referring to FIG. 1, a typical cantilever shaped SMR 1 has a microfluidic channel 2 with ports P1 and P3, whose pressure is controllable to cause fluid flow through the channel 2. A novel additional channel 3, which connects with channel 2, with it's own Port P2, is added for this embodiment of the invention. The pressure of Port P2 can be adjusted relative to P1 and P3 to either divert flow into channel 3, or cause flow from channel 3 into channel 2. Thus when a particle 4 is introduced into the carrier fluid in channel 2, the pressure at P3 may be adjusted to cause particle 4 to divert into channel 3

As shown, channel 3 may include a trap geometry smaller than the channel dimensions, sized to trap particles in a size range of interest. Thus particle 4 may be held within the SMR 1 for a long period, which enables a wide variety of potential applications which will be described herein and in other co-pending applications. When desired, the pressure at P3 may be adjusted to push particle 4 away from the trap and into the flow in channel 2 carrying the particle out of the SMR 1. This the novel SMR provides precise trapping control without the need to back flush the SMR to remove the particle as is the case in previously disclosed SMR particle traps.

Figure 2:
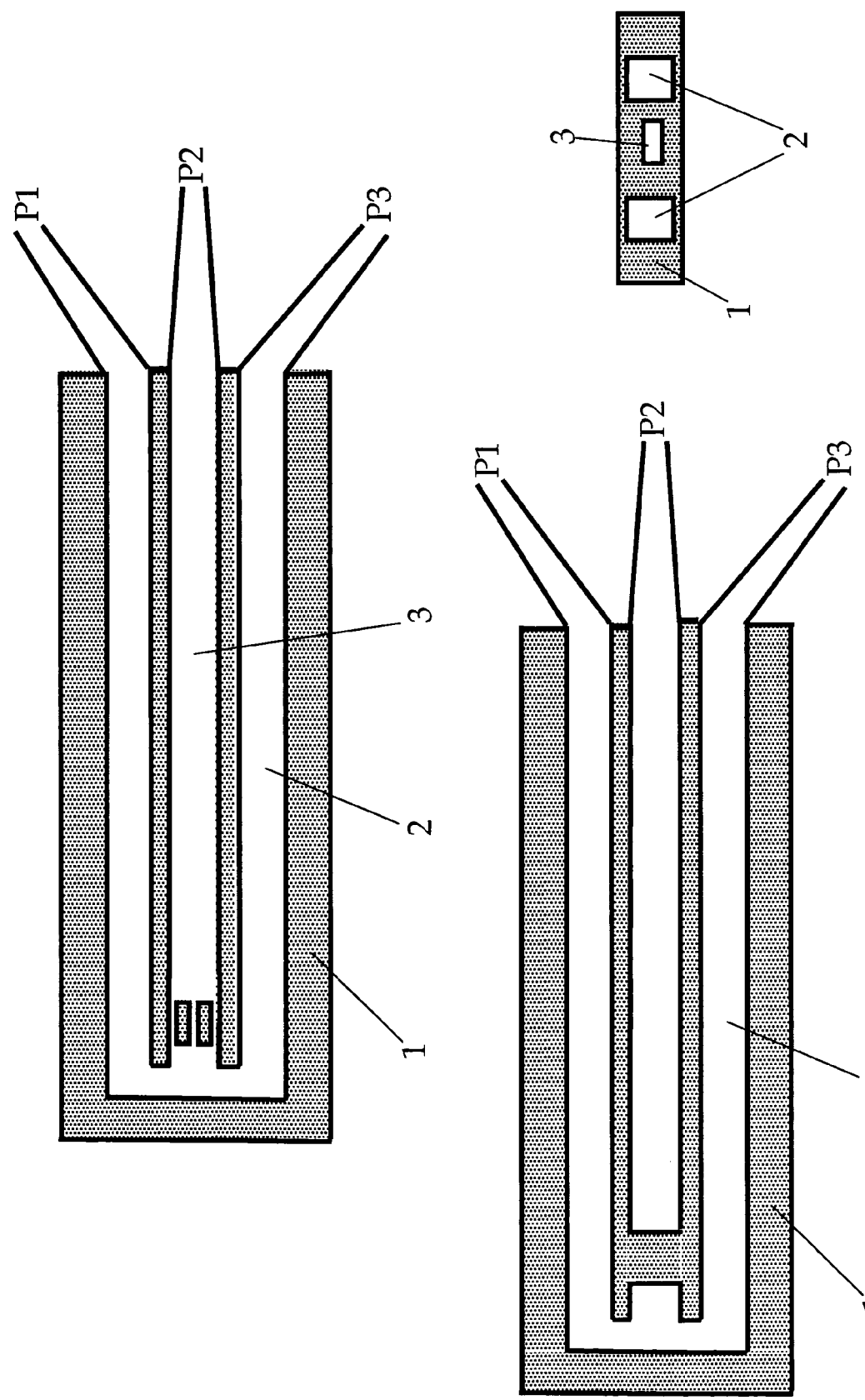
FIG. 2 depicts other trap geometries compatible with the SMR of FIG. 1.

FIG. 1 depicts the trap as a vertical slit. FIG. 2 shows other trap arrangements such as a vertical sieve and a horizontal slit. Other possible shapes and orientations for traps would also work from a functional standpoint as long as they are sized appropriately. However the micro fabrication processes used favor rectilinear features, which are oriented either vertically or horizontally to the plane of the SMR, so such arrangements are preferred. Although dimensions of the channels and traps may vary as needed within the microfabrication process design rules, channel cross section dimensions on the order of 10-20 microns, and trap dimensions with openings on the order of 1 micron have been found to be useful, particular for cells. For the case of a cantilever shaped SMR, the most sensitive measurement region is near the free end, so the traps and channels should be arranged accordingly as shown. However one skilled in the art will recognize that there is latitude in the precise placement of the structures. For other SMR geometries, the trap should be placed near the measurement sensitive region as appropriate for the geometry. Such traps are referred to by the inventors as third channel pockets.

Figure 3:
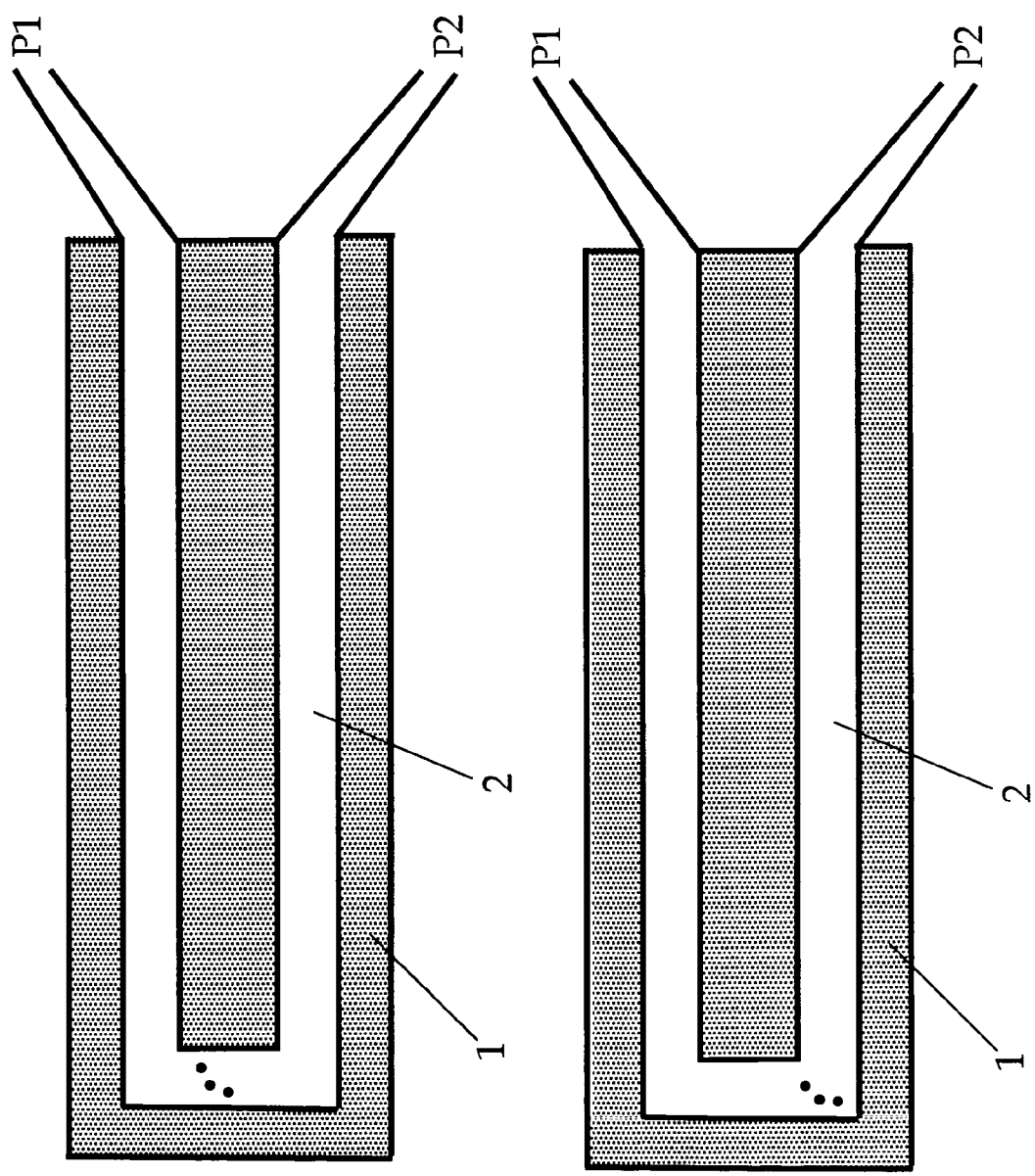
FIG. 3 is a schematic illustration of post traps according to the invention.

FIG. 3 shows another novel trap geometry used in a conventional single channel 2, two port SMR 1. In this embodiment the trap consists of one or more posts spanning a dimension of channel 2. The posts are advantageous because it's harder for softer particles such as cells to be pushed through by the applied pressure.

Figure 4:
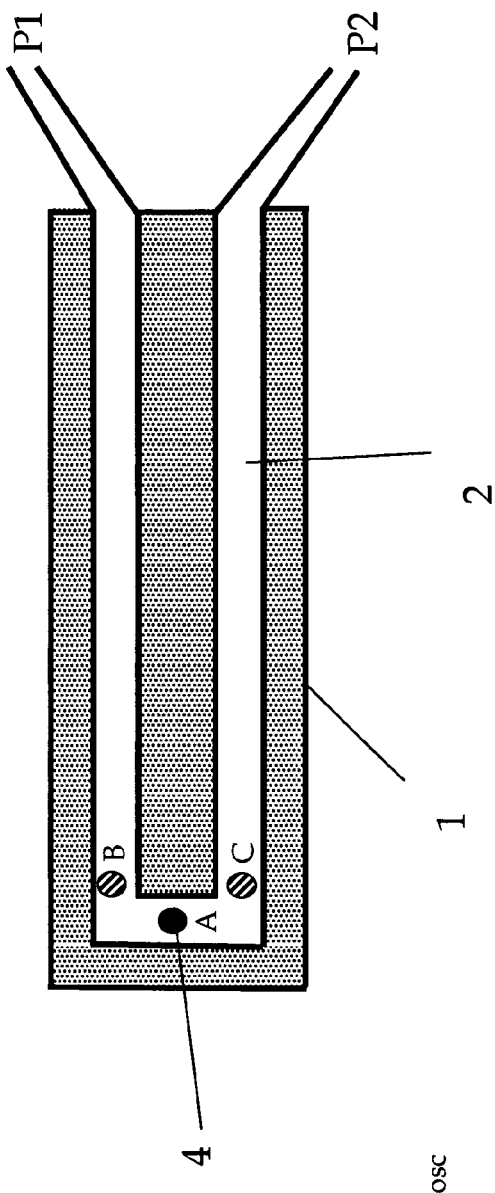
FIG. 4 is a schematic illustration of a Suspended Microchannel Resonator using flow reversal to trap a particle.
Figure 4:
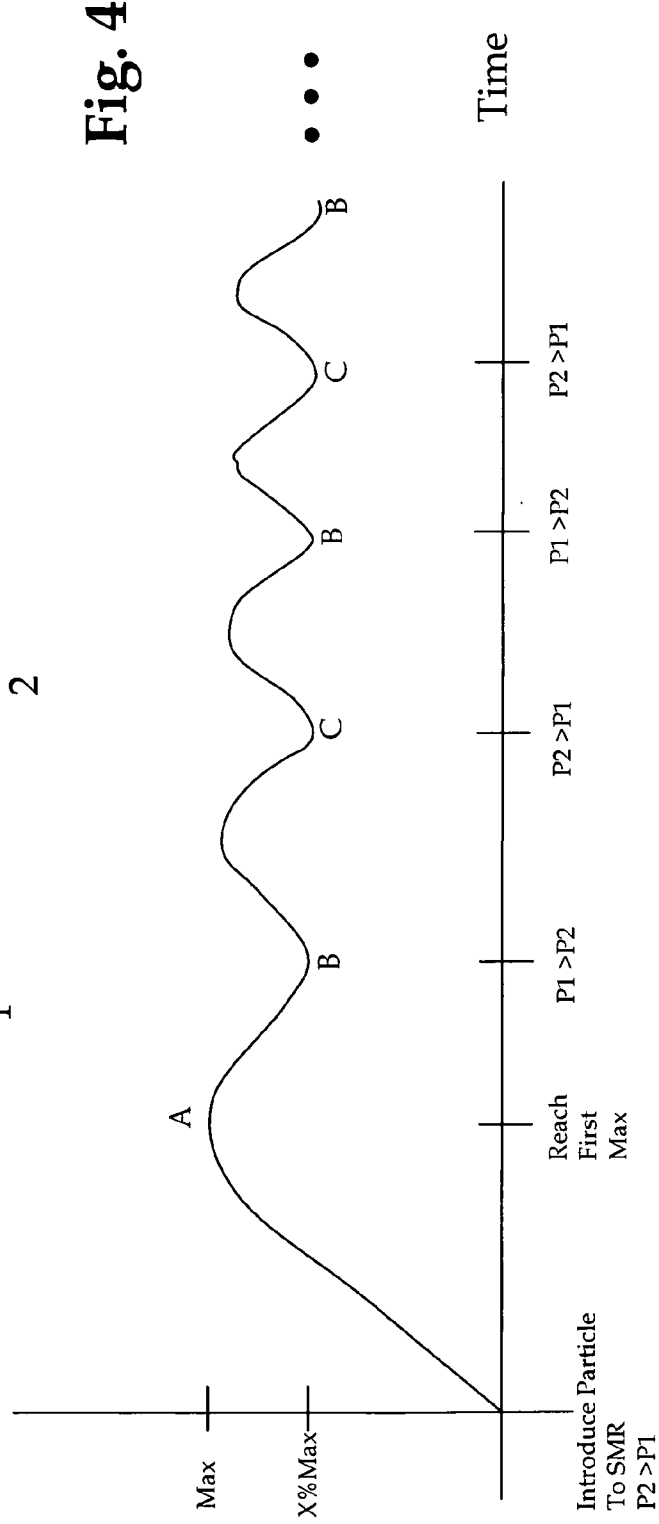

Referring to FIG. 4, another trapping system is shown. A typical cantilever shaped SMR 1 has a microfluidic channel 2 with ports P1 and P2, whose pressure is controllable to cause fluid flow through the channel 2. When a particle 4 enters channel 2 in an oscillating SMR, the effect on the oscillation will vary as the particle approaches the most sensitive region of the SMR, the effect on the oscillation amplitude will increase until the particle reaches the most sensitive measurement region, which for a cantilever SMR will be the part of the fluidic channel closest the free end. It is known in the art to detect the position of particles in an SMR in this fashion, and this technique is relied upon through out the present disclosure. As shown in the figure, once a maximum is detected, the control electronics and fluidic controls may be adapted to operate as a feedback loop. As the particle moves past the maximum delta point, a setpoint value can be chosen such that when the amplitude reaches the setpoint, the pressure on the fluid ports is reversed. This will send the particle back the other way through the max point and past to where the particle's effect will reach the setpoint going the other way, causing the control system to again reverse the pressure. Thus the particle may be kept in the measurement region for a long period of time. It is to be understood that the symmetrical approach shown in the figure is shown for simplicity, but perfect symmetry in the setpoints for instance is not required nor should be considered a limitation. Reverse pressure particle traps have been disclosed for other measurement systems such as Coulter Counters, but the particular technique for SMR's is distinct from earlier implementations, and is particularly effective.

Figure 5:
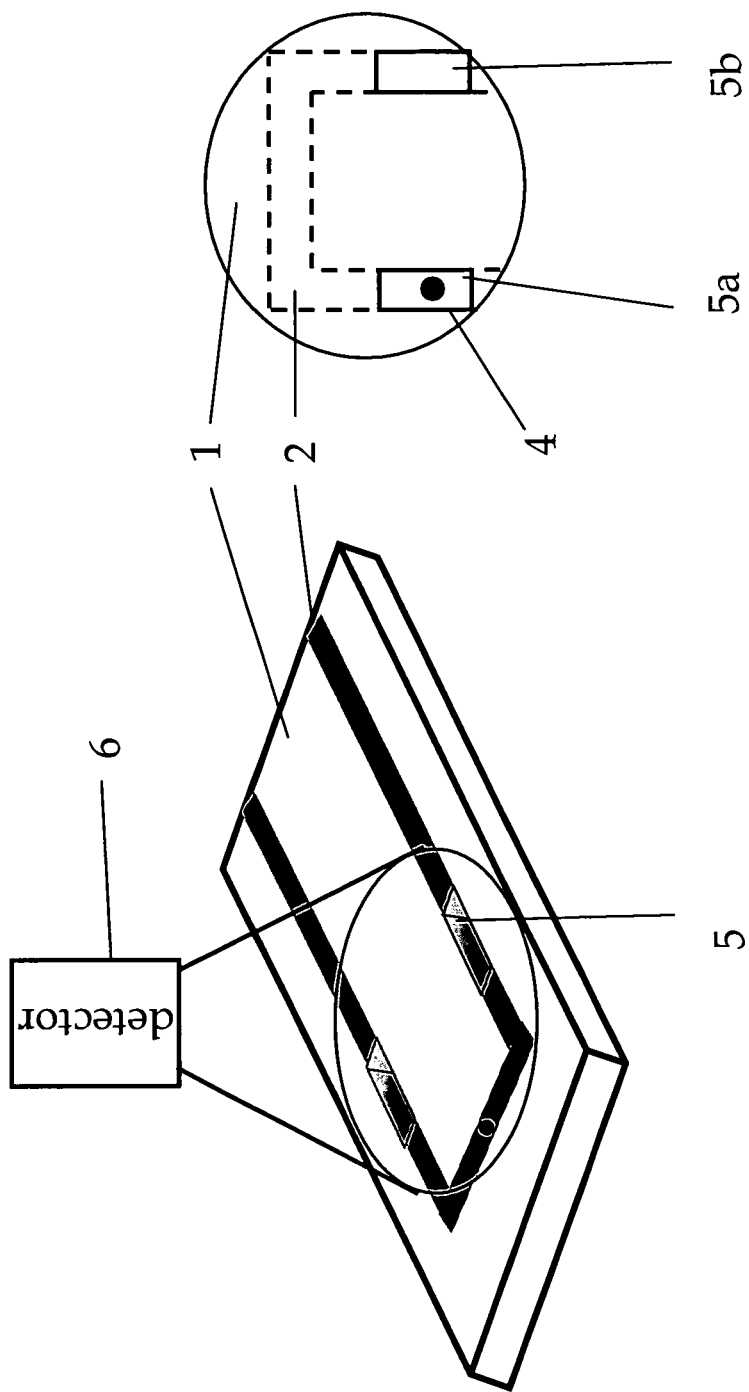
FIG. 5 is a schematic illustration of a Suspended Microchannel Resonator using an optical detector such as Charge Coupled Device, Photodiode, or Photo Multiplier Tube to sense particle position in order to reverse flow to trap a particle.

FIG. 5 depicts another trapping alternative. For suitable SMR's, which can be fabricated with windows 5, an optical detector 6 such as Charge Coupled Device, Photodiode, or Photo Multiplier Tube may be placed such that the detector monitors the particle in windows. The number, positions, and shapes of windows 5 can vary. A similar scheme of pressure control to that described in para 0018 can be coupled with the feedback from the optical detector signal instead of the oscillation signal. For example, control electronics can reverse the flow when the particle 4 is detected inside the window 5a and reverse again when it is in window 5b. By reversing the flow this way, the particle may be kept in between the two windows for a long period of time. This implementation will decouple the trapping from the oscillation signal, which enables a stable trapping in circumstances where there are other sources of oscillation signal change in addition to the one from the particle such as in mixing of two different fluids. This trapping scheme can be applied to non-sensitive regions of SMR to trap one particle as the other particle is being measured in the sensitive region.

Figure 6:
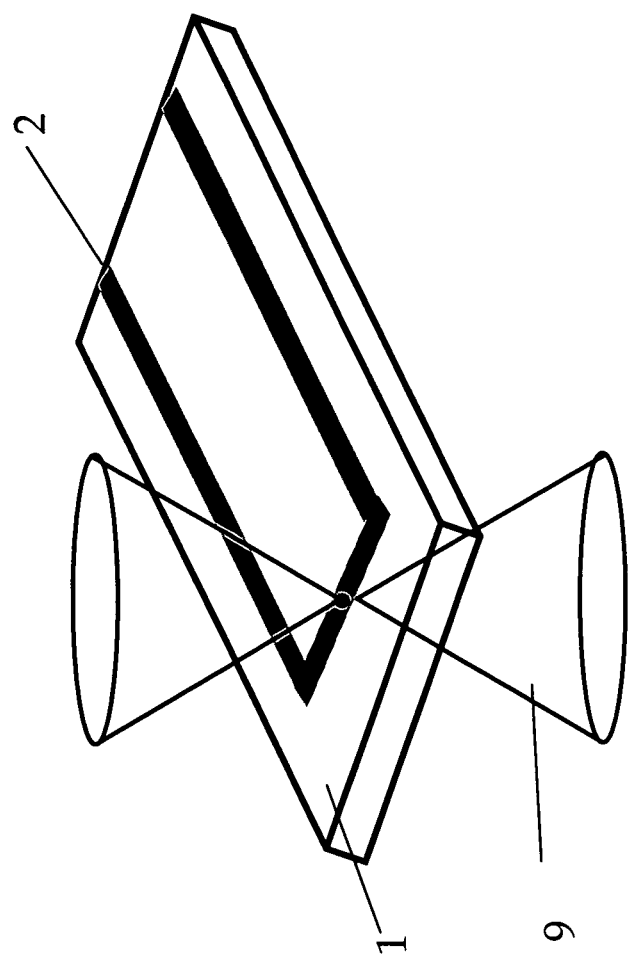
FIG. 6 shows optical tweezers used to trap a particle in the SMR.

FIG. 6 depicts another trapping alternative. For suitable SMR's, of which some varieties are transparent to some optical wavelengths, or can be fabricated with windows, optical tweezers 9 may be placed such that the tweezer active area is at the sensitive measurement point of the SMR. A particle's approach may be detected as the increasing effect on oscillation amplitude, causing the tweezers to activate and trap the particle.

Another simple trapping technique is to trap the particle inertially. A particle oscillating against an SMR channel wall will tend to slide toward the region of higher oscillation, in the case of a cantilever the part of the channel closest the end which is also the most sensitive measurement region. As the particle approaches the free end of the lever arm, it is possible to select a flow rate and an oscillation amplitude where the oscillation-induced centrifugal force pressing the particle against the channel wall creates enough friction to overcome the fluid flow, thereby trapping the particle against the wall. Typically a combination of increasing the oscillation as the particle enters the free end of the channel and/or decreasing the fluid flow over normal operating parameters will be required. The inertial trapping conditions will vary with particle characteristics and SMR geometry, and not all scenarios lend themselves to this technique, but one skilled in the art will be able to determine the parameters experimentally for a suitable scenario.

The various trapping techniques disclosed herein and the cited references have different degrees of effectiveness for different particle types. For instance the SMR third channel pocket traps work better for stiffer particles, while soft particle are more effectively trapped with the fluid reversing technique, inertial, or the optical tweezers. However the trapping is accomplished, once a cell, in particular, is trapped in an SMR, a wide range of important measurement capabilities become available.

Individual cell growth is very difficult to measure accurately with existing techniques, primarily due to the fact that although cell dimensions can be accurately measured, the mass of a cell does not necessarily correlate simply to it's volume. Thus an SMR with femtogram mass resolution is an ideal tool to very accurately observe cell mass growth (or shrinkage). Cell growth measurement is one of the drivers for developing particle trapping techniques for SMR's.

Figure 7:
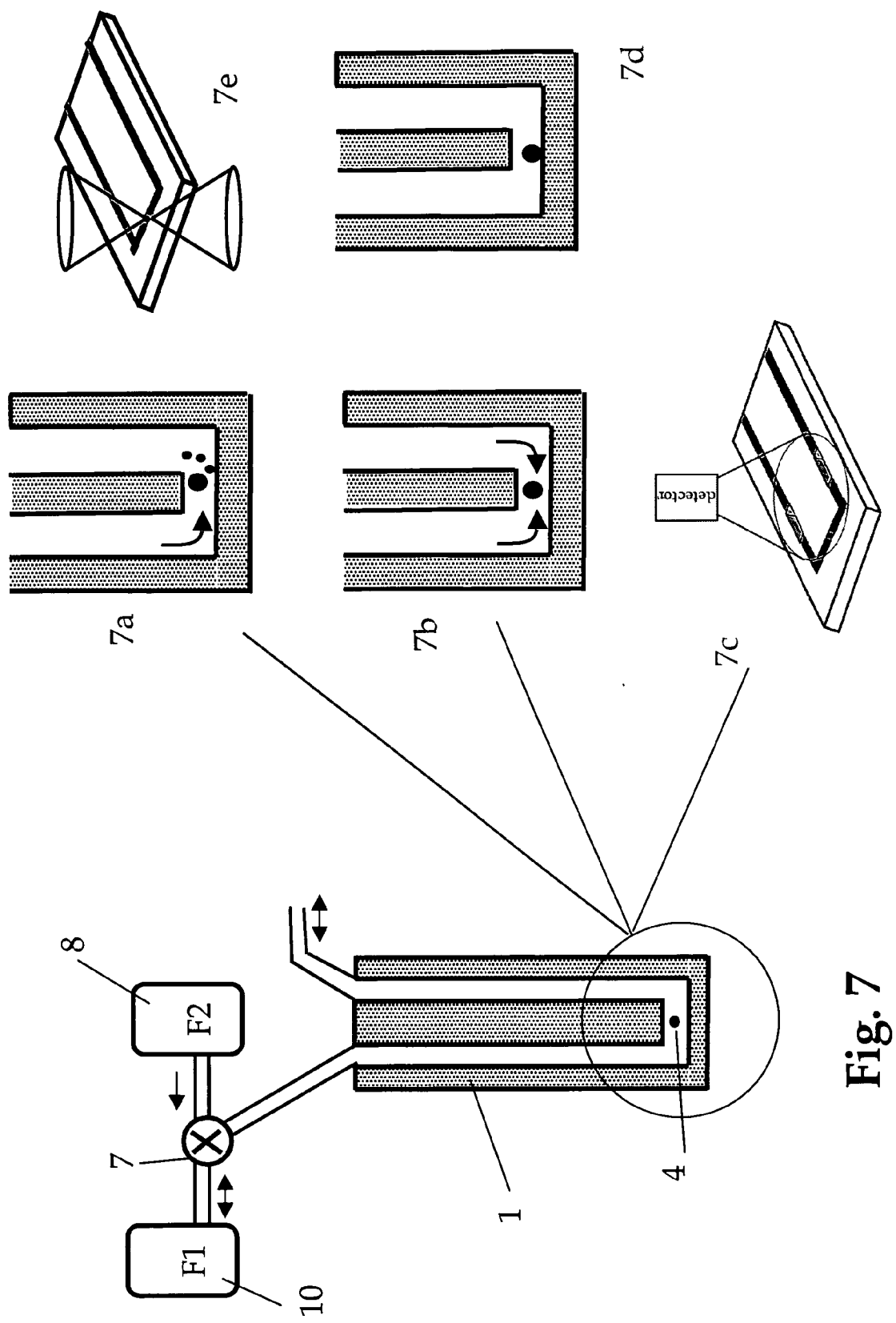
FIG. 7 depicts mixing to change the fluid environment while a particle is trapped in the SMR.

As discussed in the parent application, changing the fluid mix in the channel while a particle is trapped is possible and has been disclosed in terms of enabling density measurements. However mixing in or changing fluids while a cell is trapped also enables the measurement of cell mass change or rate of change in response to change in fluid environment. Illustrated in FIG. 7 is an SMR 1 mated with a fluidic system 7 capable of introducing two or more fluid types 10 and 8 into the SMR. This fluidic system is shown abstractly simply to illustrate the concept of having a system capable of changing the fluid characteristics external to the SMR channel. Obviously a variety of fluid handling schemes will occur to one skilled in the art, which can perform this function. Such a system may be mated with a variety of particle traps, such as a post trap 7a, a reversing flow trap from oscillation signal feedback 7b, a reversing flow trap from optical detector signal feedback 7c, an inertial trap 7d, or an optical tweezer trap 7e.

Figure 8:
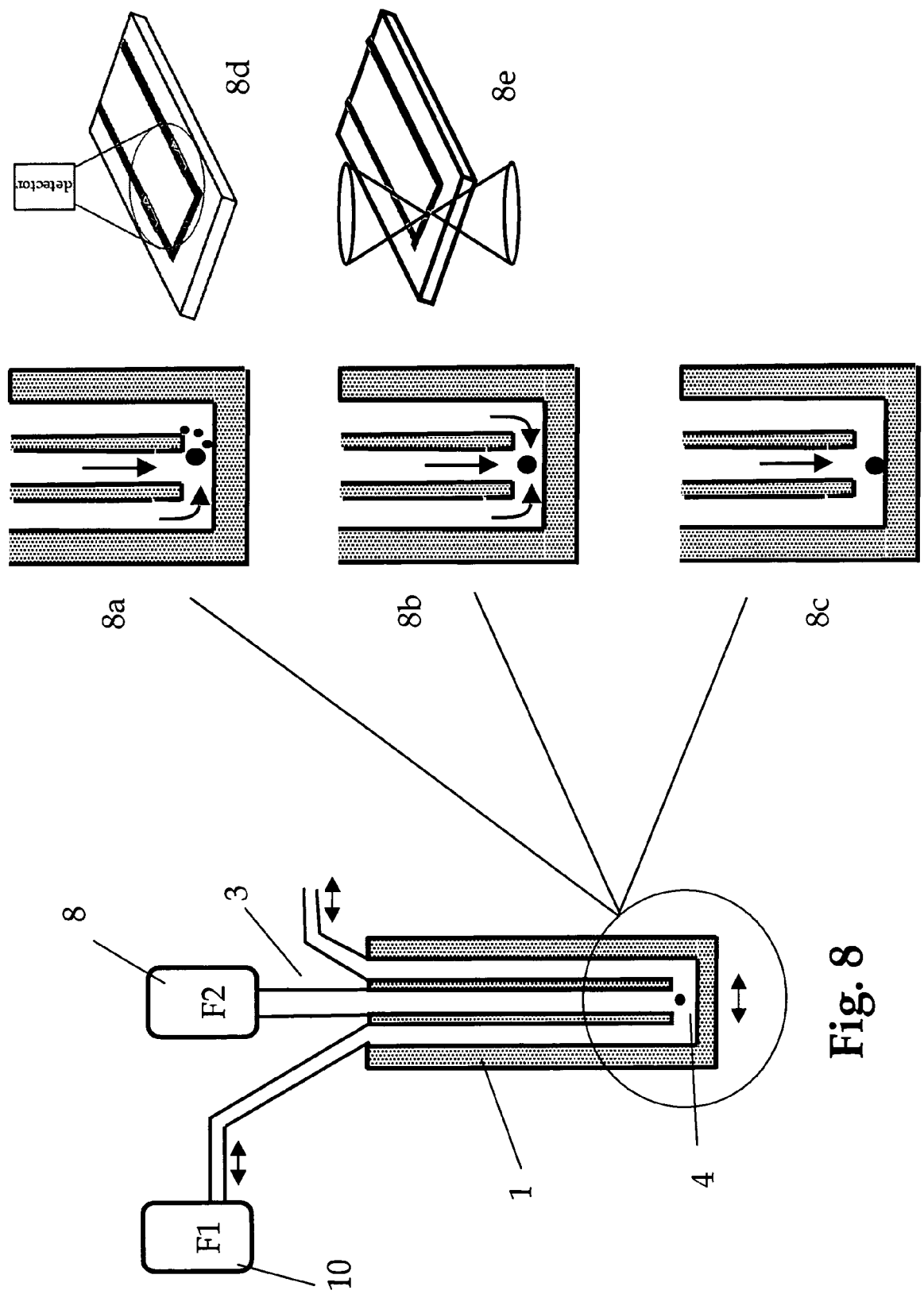
FIG. 8 shows using an SMR with an additional independently controlled channel as the mixing element.
Figure 9:
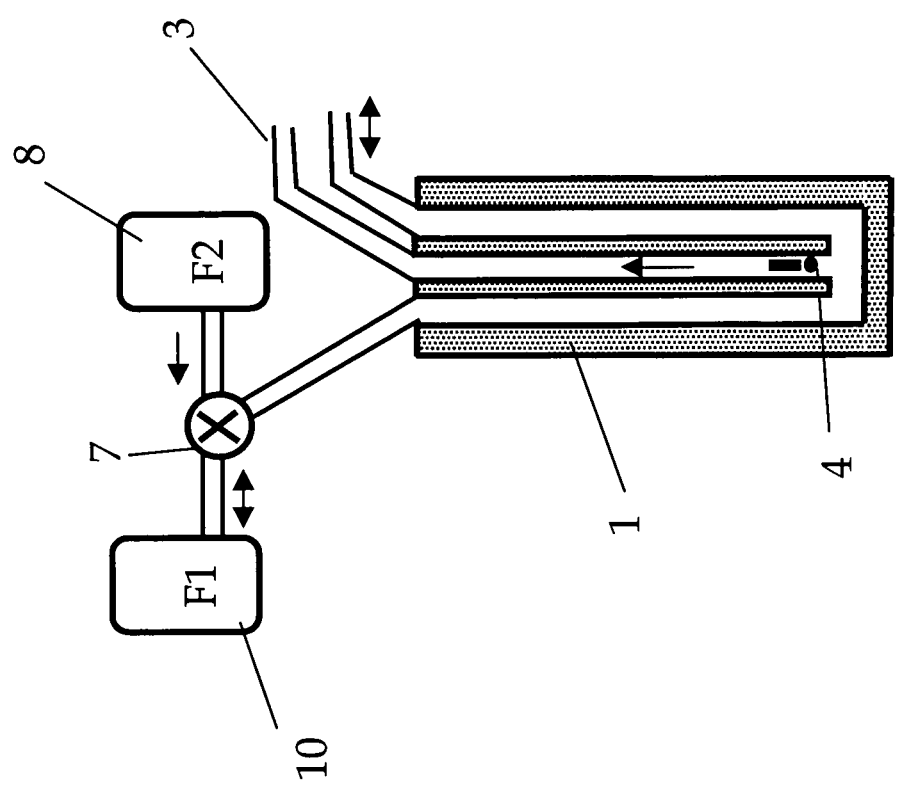
FIG. 9 depict fluid environment control in a third channel pocket trap

An alternative system for changing fluid environment is shown in FIG. 8. Particle 4 is introduced into SMR 1 in carrier 10. In this system, additional channel 3 is not used to trap the particle, but rather to introduce a fluid change 8 directly to the sensitive measurement region of the SMR. Again such a system is compatible with a variety of traps as shown As shown in FIG. 9, a third channel pocket trap 3 may trap particle 4 in an SMR system which can externally change the fluid composition 7.

Particles may also be trapped external to the active region of the SMR in a system capable of controlling delivery of the particles to the measurement region in a repeatable fashion. An exemplary system is shown in FIG. 10. In this system Bypass channel 1 is used to introduce particles into the system, bypass channel 2 transits the active region of the SMR and bypass channel 3 contains capture pockets and is connected to controllable fluid sources. All channels are independently pressure controlled at both ends. One skilled in the art will recognize that a particle may be guided through such a system, specifically directed to a pocket, captured in the pocket, released into the measurement region of the SMR, and then recaptured in the pocket, or another pocket as shown in the example Figure. Thus the particle may be measured in between periods of time spent in the pocket(s). During time in the pocket(s), the fluid characteristics may be varied.

In all variations disclosed, the ability to trap a particle for a controlled time and under a controlled fluid environment is coupled with the ability to measure the particle's mass (and/or density) in an SMR, either during or between time/environment cycles. For cells, with the SMR's potential mass resolution of 0.01%, this capability allows for extremely accurate determinations of cell mass change over time and under exposure to environmental change. A cell's growth in one carrier solution may be directly compared to it's growth in another. For instance a cell may be observed for a time in a nutrient solution and then the solution changed to include a drug or other substance, such as a chemotherapy agent, allowing for detailed information on the effectivity of the drug or the resistance of the cell.

If necessary, adjustments or calibrations of varying fluid densities as the fluidic environment is changed may be mad in ways known in the art.

The foregoing description of the embodiments of the present invention has shown, described and pointed out the fundamental novel features of the invention. It will be understood that various omissions, substitutions, and changes in the form of the detail of the systems and methods as illustrated as well as the uses thereof, may be made by those skilled in the art, without departing from the spirit of the invention. Consequently, the scope of the invention should not be limited to the foregoing discussions, but should be defined by appended claims.

What is claimed is:

1. A Suspended Microchannel Resonator (SMR) system, comprising;
    an oscillating substrate, with at least one fixed end and a region of high sensitivity away from the fixed end oscillated at or near resonance during operation; and,
    a microfluidic system built into the substrate, comprising;
    at least one fluid channel disposed between an inlet and an outlet port,
    a post trap at or near the region of high sensitivity; and,
    a fluidic delivery element disposed to modify the fluidic environment during the time period in which a particle is trapped; wherein the particle's presence is detectable by its effect on the resonant frequency of the SMR, allowing for trapping of the particle in the post trap to measure characteristics of the particle determined from its effect on the resonant frequency while trapped.

2. A Suspended Microchannel Resonator (SMR) system, comprising;
    an oscillating substrate, with at least one fixed end and a region of high sensitivity away from the fixed end oscillated at or near resonance during operation; and,
    at least one fluid channel disposed between an inlet and an outlet port,
    a post trap at or near the region of high sensitivity; and,
    an additional channel with an independent port in fluid communication with the first fluid channel, wherein fluid introduced in the additional channel mixes with the fluid in the first channel to change the fluid environment during the period when a particle is trapped; wherein the particle's presence is detectable by its effect on the resonant frequency of the SMR, allowing for trapping of the particle in the post trap to measure characteristics of the particle determined from its effect on the resonant frequency while trapped.

* * * * *